Figure 1:
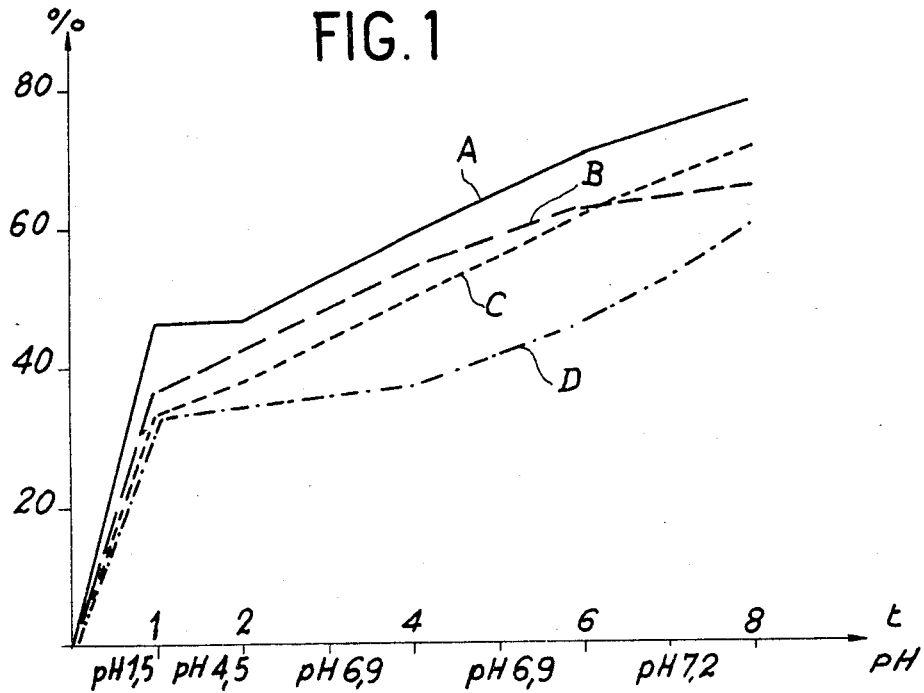

United States Patent [19]

Berthet et al.

[11] Patent Number: 4,590,068

[45] Date of Patent: May 20, 1986

[54] INERT CROSS-LINKED COPOLYMER SUPPORT, ITS PREPARATION PROCESS AND ITS USE FOR PRODUCING DELAYED ACTION MEDICAMENTS

[75] Inventors: Jeanne Berthet, Velizy Villacoublay; Marie-Francoise Blin, Versailles; Gilbert Gaussens, Meudon, all of France

[73] Assignee: Compagnie ORIS Industrie S.A., Gif sur Yvette, France

[21] Appl. No.: 525,404

[22] Filed: Aug. 22, 1983

Related U.S. Application Data

[63] Continuation of Ser. No. 278,752, Jun. 29, 1981, abandoned.

[30] Foreign Application Priority Data

Jun. 30, 1980 [FR] France .................................. 80 14529

[51] Int. Cl.$^4$ .................... A61K 31/78; C08F 220/12; C08F 220/20
[52] U.S. Cl. ......................................... 424/81; 428/402; 514/951; 526/323.1; 526/323.2; 522/84
[58] Field of Search .................. 526/317, 323.1, 323.2; 424/81; 514/951; 428/402

[56] References Cited

U.S. PATENT DOCUMENTS

| | | | |
|---|---|---|---|
| 3,080,346 | 3/1963 | Schellenberg et al. | 424/81 |
| 3,608,063 | 9/1971 | Banker | 424/81 |
| 3,881,026 | 4/1975 | Shepherd et al. | 424/81 |
| 3,959,237 | 5/1976 | Blank | 424/81 |
| 3,966,902 | 6/1976 | Chromecek | 424/81 |
| 4,234,467 | 11/1980 | Ryrfors et al. | 526/317 |
| 4,411,754 | 10/1983 | Kaetsu et al. | 424/81 |

*Primary Examiner*—Harry Wong, Jr.
*Attorney, Agent, or Firm*—James E. Nilles

[57] ABSTRACT

Inert cross-linked copolymer able to absorb and then progressively release a pharmaceutically active substance, wherein it is constituted by a powder of a cross-linked copolymer comprising 30 to 80% by weight of monounsaturated alkyl acrylate and/or methacrylate;

5 to 68% by weight of acrylic and/or methacrylic acid; and 2 to 15% by weight of bifunctional or trifunctional acrylate and/or methacrylate polymerized in accordance with free radical polymerization mechanisms.

8 Claims, 7 Drawing Figures

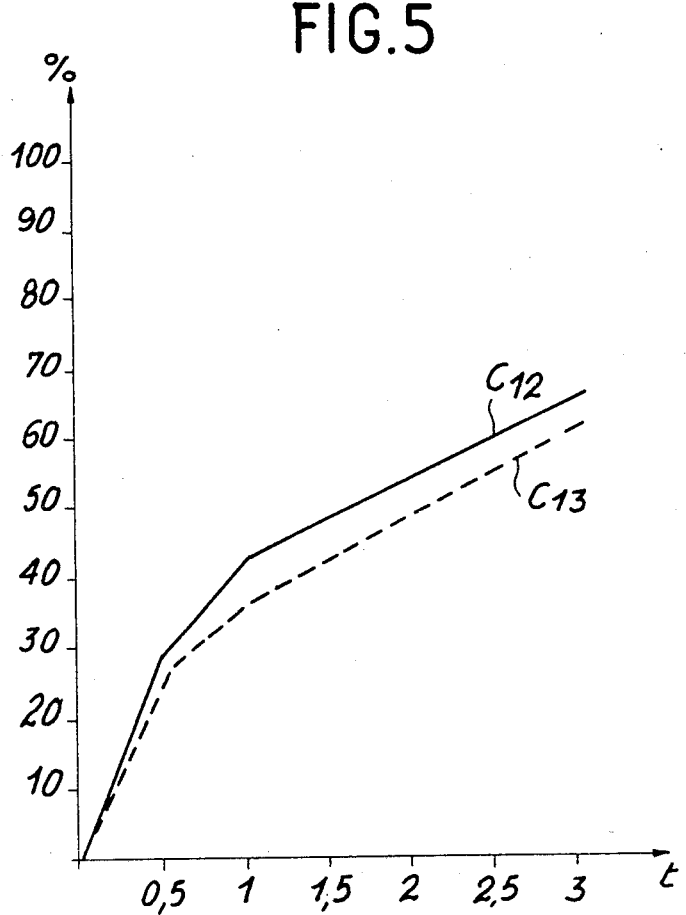

INERT CROSS-LINKED COPOLYMER SUPPORT, ITS PREPARATION PROCESS AND ITS USE FOR PRODUCING DELAYED ACTION MEDICAMENTS

This is a continuation of application Ser. No. 278,752, filed June 29, 1981, now abandoned.

The present invention relates to an inert cross-linked copolymer support able to absorb and then progressively release a pharmaceutically active substance, its preparation process and its use for producing delayed action medicaments.

Hitherto, such delayed action medicaments, i.e. medicaments able to progressively release a pharmaceutically active substance have been produced by processes consisting of coating, encapsulating or microencapsulating the pharmaceutically active substance in a material which is able to slow down the spreading or diffusion thereof into the external medium. However, these processes have the disadvantages of being difficult to perform and of not making it possible to ensure a satisfactory control of the desorption kinetics of the thus coated or encapsulated pharmaceutically active substance.

In addition, French Patent EN No. 73 40002 of Nov. 9th 1973 discloses a process for producing products able to release a chemical substance based on the use of hydrophobic polymer supports incorporating polymerized hydrophilic inclusions and grafted onto the hydrophobic polymer. In this case, the substance is stored in the support by absorption from a solution, which constitutes an advantage compared with the coating or encapsulating processes because it is easier to perform the storage stage. Moreover, the use of the supports makes it possible to more easily control the desorption kinetics of the substance retained by the support.

The present invention relates to inert cross-linked copolymer supports able to retain and then progressively release a pharmaceutically active substance which, due to their special composition, provide improved properties compared with the aforementioned polymer supports. This more particularly relates to their capacity of absorbing the substance and their possibility of controlling the desorption kinetics of the retained substance.

The invention also relates to cross-linked copolymer supports which are particularly suitable for the retention of pharmaceutically active substances such as codeine and ketoprofen, i.e. 2-(3-benzoylphenyl)-propionic acid.

According to the invention, the inert cross-linked copolymer support able to absorb and then progressively release a pharmaceutically active substance is characterized in that it is constituted by a powder of a cross-linked copolymer comprising:

30 to 80% by weight of monounsaturated alkyl acrylate and/or methacrylate:

5 to 68% by weight of acrylic and/or methacrylic acid; and 2 to 15% by weight of bifunctional or trifunctional acrylate and/or methacrylate.

According to the invention alkyl radicals of the monounsaturated alkyl acrylates or methacrylates have one to twelve carbon atoms.

Advantageously, the monounsaturated alkyl acrylate or methacrylate monomers are chosen from the group consisting of butyl, hexyl and heptyl acrylates and methyl, ethyl, butyl, hexyl and heptyl methacrylates.

According to the invention, the term bifunctional or trifunctional acrylate or methacrylate means an ester comprising two or three double bonds.

Examples of bifunctional esters which can be used are diethylene glycol diacrylate, tetraethylene glycol diacrylate and polyethylene glycol diacrylate.

Examples of trifunctional acrylic or methacrylic esters which can be used are trimethylol propane triacrylate and trimethylol propane trimethacrylate.

Preferably, the copolymer contains 30 to 80% butyl methacrylate, 5 to 68% acrylic acid, and 2 to 15% trimethylol propane trimethacrylate or triacrylate or tetraethylene glycol diacrylate.

According to the invention, when the support is intended for producing orally or rectally administrable delayed action medicaments, the powder is in the form of particles with a grain size distribution such that they are not held back in the folds or walls of the intestines.

From the practical standpoint, the average size of the particles is below 700 $\mu$m and above 20 $\mu$m and more particularly within a range of 100 to 400 $\mu$m when the support is intended for producing orally administrable medicaments and 20 to 50 $\mu$m when it is intended for producing rectally administrable medicaments.

The invention also relates to a process for the preparation of such an inert cross-linked copolymer support.

This process is characterized in that a mixture of acrylic and/or methacrylic monomers comprising a monounsaturated alkyl acrylate and/or methacrylate, acrylic and/or methacrylic acid, and bifunctional or trifunctional acrylate and/or methacrylate is polymerized in accordance with a free radical polymerization mechanism. Preferably, polymerization is carried out in emulsion under ionizing radiation.

Advantageously, the thus obtained cross-linked copolymer undergoes complementary irradiation by means of ionizing rays in order to adapt its degree of cross-linking.

The integrated irradiation dose used for performing polymerization and cross-linking is generally approximately 0.9 to 8 Mrad, i.e. 9000 to 80,000 Gy.

The supports according to the invention can be used for producing delayed action medicaments.

For producing such medicaments, a pharmaceutically active substance is kept in contact with the cross-linked copolymer support in particle form for a time which is sufficient for bringing about the absorption of the desired quantity of active substance on and in the support.

Preferably, the particles of the support are kept suspended within the solution, preferably an aqueous or alcoholic solution of the pharmaceutically active substance which advantageously contains 10 to 60 mg of substance/100 ml for a time sufficient to ensure the absorption of the desired quantity of said substance. The solution is then eliminated and the particles of the support having retained or held back the pharmaceutically active substance are dried or lyophilized until a constant weight is obtained for eliminating the solvent absorbed in the support.

Other characteristics and advantages of the invention will become apparent from reading the following description and from the illustrative and non-limitative examples, as well as the attached FIGS. 1 to 7 which are graphs illustrating the progressive release of the pharmaceutically active substance as a function of time (in hours).

The following or an equivalent procedure is used for preparing the inert polymer supports able to absorb and then progressively release a pharmaceutically active substance in accordance with the present invention.

The cross-linked polymer structure serving as the support is produced either by mass polymerization or emulsion polymerization, preferably under ionizing irradiation.

In the first case, an adequate quantity of each of the two aforementioned monomers, i.e. monounsaturated acrylic and/or methacrylic monomers and bifunctional or trifunctional acrylic and/or methacrylic monomers, under a vacuum of at least $10^{-2}$ Torr or under a nitrogen atmosphere, to ionizing irradiation, e.g. by means of UV, X, $\alpha$, $\beta$ or $\gamma$ rays or to accelerated electron beams, particularly $\gamma$ radiation. This leads to the polymerization and cross-linking due to the polyfunctional monomer able to create a three-dimensional network.

In the second case, an emulsion of the organic phase constituted by the mixture of the monomers is prepared in a weakly acid aqueous phase of pH close to 3 or 4 and which contains in solution a salt, particularly sodium salt at its maximum concentration for preventing the passage of the water-soluble monomers into said aqueous phase. The aqueous phase also contains an agent which inhibits the polymerization of the monomers, particularly Mohr's salt, as well as an agent assisting the formation of the emulsion and in particular polyacrylic acid. The weight ratio of the aqueous phase to the organic phase is close to 1. The emulsion is obtained very rapidly by energetically mixing the aqueous and organic phases at ordinary temperature.

As in the first case, the emulsion undergoes ionizing irradiation for carrying out polymerization and cross-linking, $\gamma$ radiation once again being used with particular advantage.

In both types of polymerization, the polyfunctional monomer quantity used is advantageously 2 to 15% by weight of the total mass of the monomers undergoing irradiation.

The dose rate applied is advantageously approximately 0.1 to 0.25 Mrad/hours. The integrated dose necessary for carrying out polymerization and cross-linking is approximately 0.9 to 8 Mrad. Cross-linking takes place under the action of ionizing radiation and the bifunctional or trifunctional acrylic and/or methacrylic monomer.

The degree of cross-linking on which the quantity of active substance is obtained and the programming or pattern of the progressive release thereof depend is a function of the chosen value for the integrated dose of ionizing radiation applied.

It is difficult to give a law applying to all cases and consequently the degree of cross-linking, i.e. the integrated dose which has to be applied to retain a given quantity of active substance per unit of support mass must be determined case by case and by preliminary tests for given monomers and a given active starting substance. Hereinafter will be given in a illustrative manner for a given copolymer an example of the variation of the degree of cross-linking illustrated by the quantity of active substance retained and by the shape of the desorption curves, i.e. the progressive release thereof for different integrated doses applied.

Once polymerization and cross-linking are at an end, when necessary the copolymer is pulverised and the fraction having the appropriate grain size is separated by screening. This fraction may, for example, have a grain size of 20 to 700 microns and particularly 200 to 400 microns when the support is intended for the production of orally administered drugs or 20 to 50 microns when the support is intended for the production of rectally administered drugs.

These powder supports can then be used for the preparation of delayed action medicaments. In this case, the active substance is absorbed in the structure of the support in the following way.

An accurately predetermined quantity of copolymer particles is kept suspended for 2 to 120 hours, preferably at a temperature of 20° to 75° C. in a solution of the active substance in water or alcohol, the weight ratio of the copolymer in g/volume of active substance solution in ml being $\frac{1}{2}$ to 1/25 and the active substance concentration of the solution being 10 to 60 g/100 ml.

After this operation, the suspension is filtered to separate the particles from the solution support. The solvent is then eliminated by drying these particles in the oven at a temperature such that the active substance is not degraded and until a constant weight is obtained.

In order to illustrate the efficacy of the galenic form of the delayed action medicament obtained in this way, the desorption kinetics of the active substance are determined and this can be carried out at a variable pH simulating the passage through the digestive system or at a fixed pH. Examples of the desorption kinetics are given hereinafter.

Preferably, the release rates of the pharmaceutically active substance as a function of time and the pH value are, in the case of coding:
contact 1 hour at pH 1.5
  30% < release < 45%
contact 1 hour at pH 1.5
  +1 hour at pH 4.5
  +2 hours at pH 6.9
  60% < release < 70%
  +1 hour at pH 1.5
  +1 hour at pH 4.5.
  +4 hours at pH 6.9
  +2 hours at pH 7.2
  release > 70%

It has also been shown and as will be also be illustrated hereinafter, the active substances retained in said delayed action medicaments undergo no chemical deterioration.

These orally and rectally administrable delayed action medicaments are advantageously in the form of gelatin capsules or suppositories containing the necessary quantity of pharmaceutically active substance.

The following examples illustrate the invention and relate to advantageous embodiments.

EXAMPLE 1

(a) Preparation of the Cross-linked Polymer Support

An emulsion of the mixture of the following monomers (organic phase) 55 parts by weight of butyl methacrylate, 35 parts by weight of acrylic acid and 10 parts by weight of trimethylol propane trimethacrylate in an aqueous phase formed by 30% by weight of sodium sulphate in 70% by weight of a 0.01N sulphuric acid solution to which is added a quantity of Mohr's salt corresponding to 2% of the acrylic acid quantity present in the organic phase is exposed to a dose rate of 0.224 Mrad/hour at ambient temperature in a Pyrex reactor equipped with a stirring mechanism and under a nitrogen atmosphere (scavenging).

The weight of the aqueous phase to the organic phase is equal to 1.

The emulsion is initiated by the addition of 0.5% by weight, based on the weight of the aqueous phase, of polyacrylic acid added to the emulsion in the form of a powder of grain size 200 to 400 microns. Polymerization requires an integrated dose of 0.9 Mrad. Cross-linking is improved by supplementary irradiation processes.

Cross-linked copolymers corresponding to the following complementary integrated doses are prepared:
1 Mrad
2 Mrad
4 Mrad.

Following irradiation, the copolymer particles obtained are dried and the particle fraction with a grain size of 250 to 400 μm is separated.

(b) Absorption of Codeine

A suspension of 1 gram of the thus obtained copolymer particles with a grain size of 250 to 400 μm in a solution of 20 g/100 ml of codeine in a water/methanol mixture in proportions 9/1 is kept stirred for 5 hours at a temperature close to 60° C.

The codeine quantities absorbed are as follows:
Cross-linked copolymer A (irradiation 0.9 Mrad) 29% by weight based on the end product.
Cross-linked copolymer B (irradiation 1.9 Mrad) 35.5% by weight based on the end product.
Cross-linked copolymer C (irradiation 2.9 Mrad) 40% by weight based on the end product.
Cross-linked copolymer D (irradiation 4.9 Mrad) 41.5% by weight based on the end product.

(c) Desorption at Variable pH

For the purposes of this experiment, a 0.1 g sample of particles of each of the copolymers A to D is kept suspended by a reciprocating stirring action for the times indicated hereinafter. This takes place successively in four solutions of respectively increasing pH value and at a temperature of 37 c±2° C.:
first solution at pH 1.5 for the first hour
second solution at pH 4.5 for the second hour
third solution at pH 6.9 for the third, fourth, fifth and sixth hours
fourth solution at pH 7.2 for the seventh and eighth hours.

The solutions are samples at each pH value change and the active substance concentration is determined by spectrophotometry.

The solutions with the different pH values are prepared from HCl and 1N NaOH in the case of that with a value of 1.5 and from monobasic potassium phosphate and 1N HCl in the case of those of pH 4.5, 6.9 and 7.2.

The result of this desorption is illustrated by curves A to D (corresponding respectively to copolymers A to D) of FIG. 1 representing the variation of the quantity of active substance (expressed as % by weight compared with the total quantity of active substance) desorbed as a function of time t (in hours) and the pH value.

On examining these curves, it can be seen that the desorption rate decreases when the irradiation dose increases.

Six other examples are given in which the active substance is codeine.

EXAMPLE 2

The polymer has the following composition: 35% butyl methacrylate, 55% acrylic acid and 10% trimethylol propane trimethacrylate, whilst its grain size is 250 to 400 microns.

It was obtained by mass polymerization in vacuo at a dose rate of 0.1 Mrad/h$^{-1}$, the irradiation dose being 2.4 Mrad.

The experimental conditions of the absorption phase are as follows:
polymer quantity: 1 gram
solution volume: 8 ml
solvent: ethanol
codeine concentration: 22 g/100 ml
duration: 18 hours
temperature: 50° C.
The codeine quantity absorbed is 54%.

Figure 2:
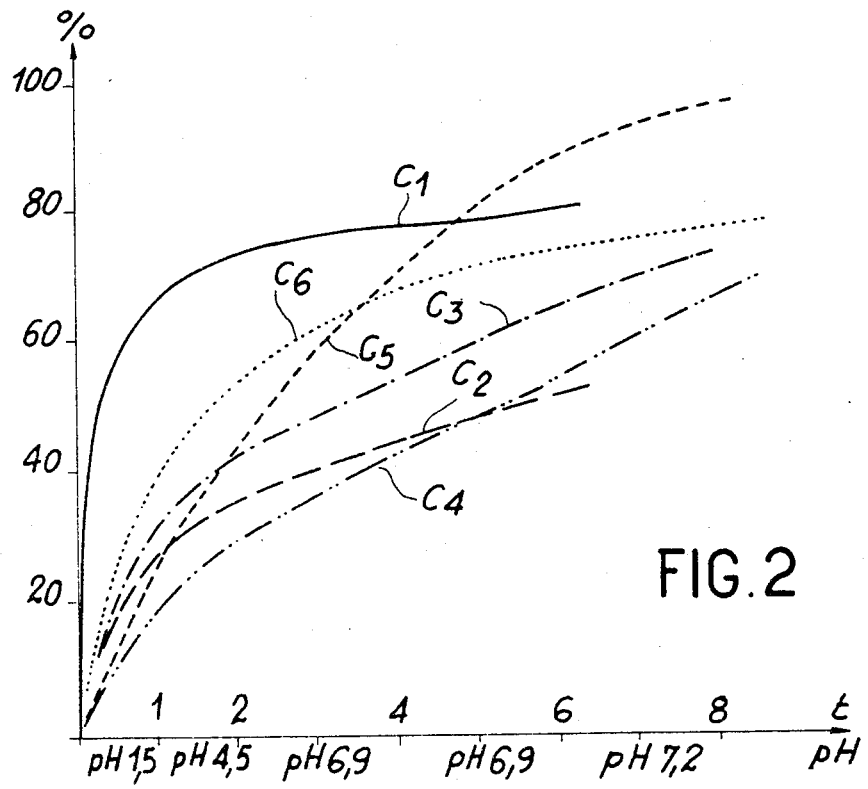

The desorption kinetics, with a variable pH are represented by curves $C_1$ in FIG. 2.

EXAMPLE 3

The polymer composition is 55% butyl methacrylate, 35% acrylic acid and 10% trimethylol propane trimethacrylate, whilst its grain size is 250 to 400 microns. The polymerization conditions are as in example 2. The experimental conditions of the absorption phase are identical to those of example 2.

The desorption kinetics at a variable pH value are represented by curve $C_2$ of FIG. 2.

EXAMPLE 4

The polymer has the following composition: 55% butyl methacrylate, 35% acrylic acid and 10% trimethylol propane trimethacrylate, whilst its grain size is 250 to 400 microns. The polymerization conditions are as in example 2.

The experimental of the absorption phase are as follows:
polymer quantity: 1 gram
solution volume: 8 ml
solvent: water
codeine concentration: 12.5 g/100 ml
duration: 3 hours
temperature: 75° C.
The codeine quantity absorbed in 45.5%.

The desorption kinetics at variable pH value are represented by curve $C_3$ of FIG. 2.

EXAMPLE 5

The polymer has the following composition: 55% butyl methacrylate, 35% acrylic acid and 10% trimethylol propane trimethacrylate, whilst its grain size is 250 to 400 microns. The polymerization conditions are as defined in example 2.

The experimental conditions of the absorption phase are as follows:
polymer quantity: 1 gram
solution volume: 4 ml
solvent: water/ethanol: 9/1
codeine concentration: 20 g/100 ml
duration: 6 hours
temperature: 60° C.
The codeine quantity absorbed is 36%.

The desorption kinetics at variable pH value are represented by curve $C_4$ of FIG. 2.

EXAMPLE 6

The polymer has the following composition: 57.5% butyl methacrylate, 37.5% acrylic acid and 5% trimethylol propane trimethacrylate, whilst its grain size is 200 to 400 microns. The polymerization conditions are the same as in example 2.

The experimental conditions of the absorption phase are identical to those described in example 2, except that the temperature is 37° C.

The codeine quantity absorbed is 47%. The desorption kinetics at variable pH value are represented by curve $C_5$ of FIG. 2.

EXAMPLE 7

The polymer of the same composition and grain size as described in example 6 received a supplementary irradiation dose corresponding to 5 Mrad.

The experimental conditions of the absorption phase are the same as those in example 6.

The codeine quantity absorbed reaches 60.5%. The desorption kinetics at variable pH value are represented by curve $C_6$ of FIG. 2.

In the case of examples 3, 4, 5 and 6, gas chromatography has shown that after desorption there is no chemical change to the codeine which has been retained in and on the support.

Seven other examples will now be given in which the active substance is ketoprofen.

EXAMPLE 8

A mixture of the following monomers: 75 parts by weight butyl methacrylate, 15 parts by weight acrylic acid and 10 parts by weight tetraethylene glycol diacrylate undergoes mass polymerization under $\gamma$ radiation of cobalt 60 (dose rate 0.12 Mrad/$h^{-1}$ and irradiation dose 2.6 Mrad).

Ketoprofen absorption takes place on a grain size fraction of 200 to 400 microns under the following conditions:
50% alcoholic solution of ketoprofen
absorption time: 24 hours
absorption temperature: 20° C.
absorption rate: 27.5% of ketoprofen.

Figure 3:
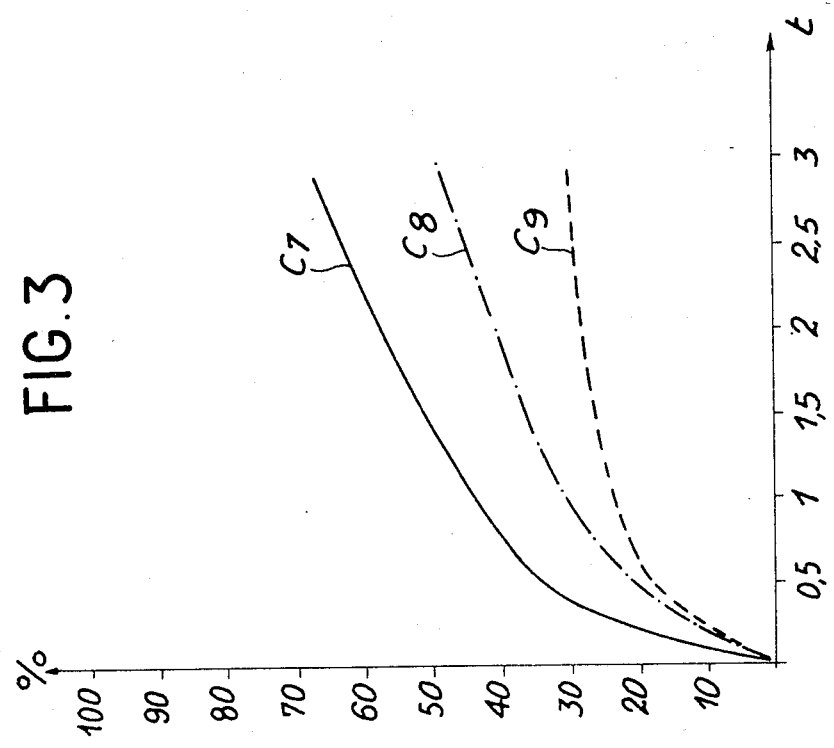
Figure 6:
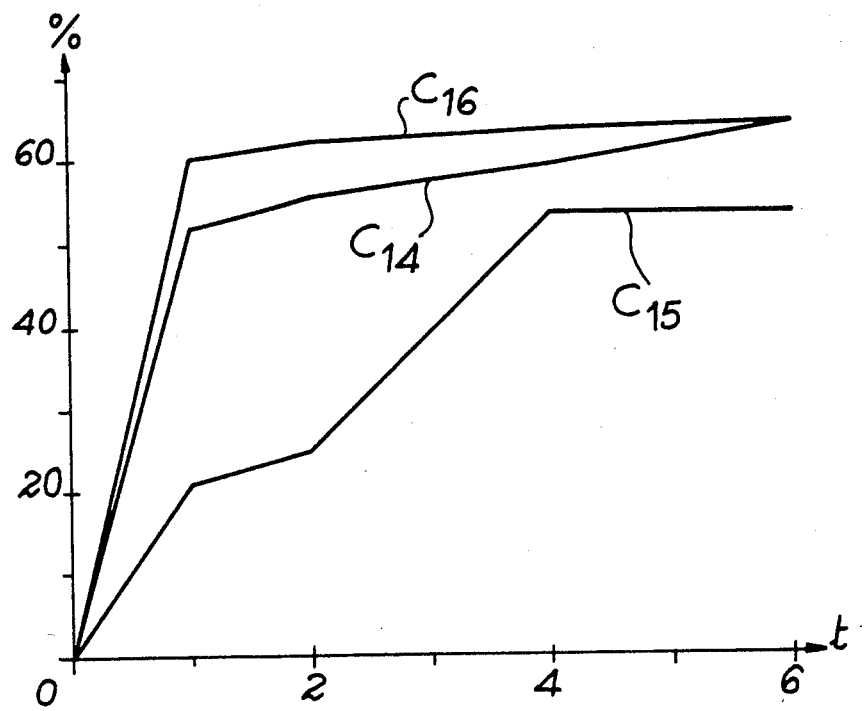
Figure 7:
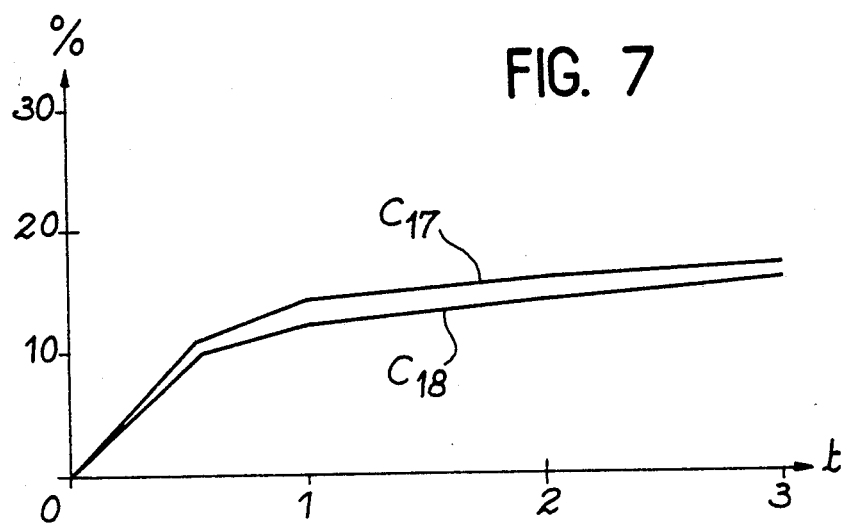

Desorption at a constant pH of 7.4 is represented by curve $C_7$ of FIG. 3.

EXAMPLE 9

Polymerization under $\gamma$ radiation of the cobalt 60 of the following mixture of monomers is carried out under the conditions of example 8: 75 parts by weight of butyl methacrylate, 15 parts by weight of acrylic acid and 10 parts by weight of polyethylene glycol diacrylate.

Ketoprofen absorption takes place under the same conditions as those of example 8 on a powder with a grain size of 200 to 400 microns. The absorption rate is 20% of ketoprofen.

The desorption kinetics at constant pH of 7.4 are represented by curve $C_8$ of FIG. 3.

EXAMPLE 10

This example corresponds to example 9, except that the polyethylene glycol diacrylate is replaced by trimethylol propane triacrylate.

The absorption rate is 20% of ketoprofen. The desorption kinetics at constant pH of 7.4 are represented by curve $C_9$ of FIG. 3.

EXAMPLE 11

The mixture of the following monomers, 79 parts by weight of butyl methacrylate, 16 parts by weight of acrylic acid and 5 parts by weight of trimethylol propane triacrylate undergoes polymerization under $\gamma$ radiation of cobalt 60 (conditions of example 8).

Ketoprofen absorption on a grain size fraction of 200 to 400 microns is performed in the following way:
50% ketoprofen alcoholic solution
absorption time: 17 hours
absorption temperature: 37° C.
absorption rate: 32% of ketoprofen.

Figure 4:
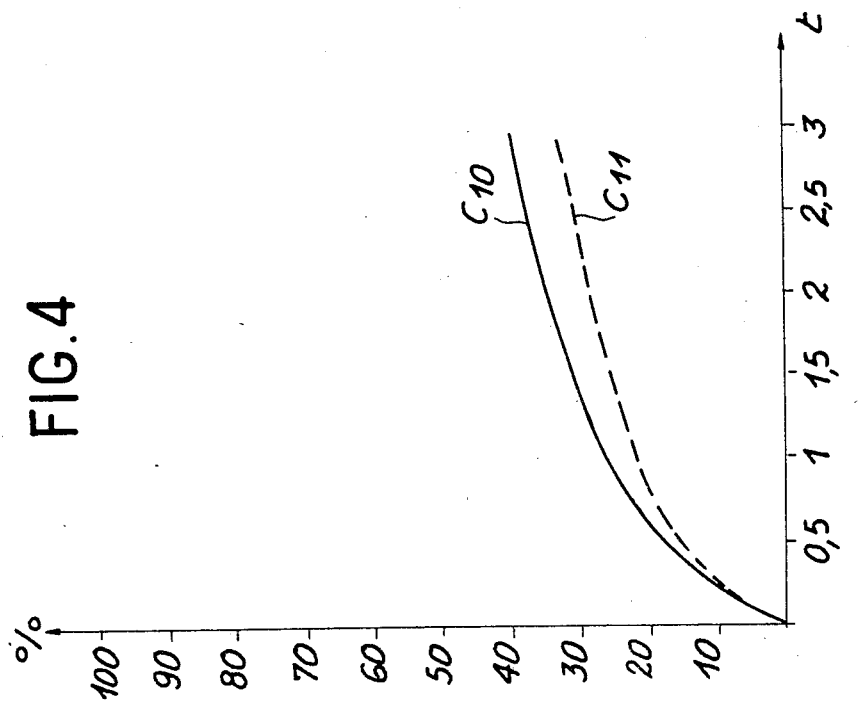

The desorption kinetics at a constant pH of 7.4 are represented by curve $C_{10}$ of FIG. 4.

EXAMPLE 12

Polymerization and absorption are carried out under the same conditions as in example 11, but the trimethylol propane triacrylate is replaced by trimethylol propane trimethacrylate.

The absorption rate is 32% of ketoprofen.

The desorption kinetics at a constant pH of 7.4 are represented by curve $C_{11}$ of FIG. 4.

EXAMPLE 13

The mixture of the following monomers: 76.5 parts by weight of butyl methacrylate, 15.5 parts by weight of acrylic acid and 8 parts of tetraethylene glycol diacrylate undergoes polymerization under $\gamma$ radiation of cobalt 60 (dose rate 0.14 Mrad/$h^{-1}$ and irradition dose 3.4 Mrad).

The ketoprofen absorption takes place under the conditions of example 12 on a powder with the grain size fraction 200 to 400 microns.

The absorption rate is 26% of ketoprofen. The desorption kinetics at constant pH of 7.4 are represented by curve $C_{12}$ of FIG. 5.

EXAMPLE 14

The mixture of the following monomers: 55 parts by weight of butyl methacrylate, 15 parts by weight of acrylic acid and 10 parts by weight of tetraethylene glycol diacrylate undergoes polymerization under $\gamma$ radiation of cobalt 60 (conditions of example 13).

Ketoprofen absorption takes place under the same conditions as in example 12, the copolymer powder having a grain size of 200 to 400 microns.

The ketoprofen absorption rate is 23%. The desorption kinetic at a constant pH of 7.4 is represented by curve $C_{13}$ of FIG. 5.

Examination of curves $C_1$ to $C_6$ (desorption at variable pH) and $C_7$ to $C_{13}$ (desorption at constant pH) illustrates that it is possible to adapt to the therapeutic requirements of the given pharmaceutical active ingredients by acting on the cross-linking of the polymers produced under ionizing radiation and cross-linked by means of the combined action mechanisms of the radiation and the polyfunctional monomers, the variable dose and dose rate of the radiation applied make it possible to progressively adapt the degree of cross-linking of the polymer network.

The curves of the codeine desorption rates performed at variable pH values attempt to reflect the conditions encountered during passage through the intestines. The desorption kinetics obtained from polymers produced according to the operating procedures of examples 6, 5, 4 and 1 and tested under energetic stirring conditions in a test of the type known in the art as a diffutest, particularly a EURAND diffutest conventionally used by the pharmaceutical industry meet the standards expected for such codeine-based delayed action medicaments.

The curves of the ketoprofen desorption rates obtained with a fixed pH are high-speed tests which galenic pharmacists are able to interpret and correlate with the in vivo behaviour of the medicament. Thus, the curves obtained from the samples produced according to the operating procedure of examples 8, 13 and 14 were considered satisfactory for a therapeutic use of the delayed release ketoprofen.

EXAMPLE 15

The polymer has the following composition: 45% heptyl methacrylate, 45% acrylic acid and 10% trimethylol propane trimethacrylate, whilst its grain size is 250 to 400 microns.

It was obtained by mass polymerization in vivo at a dose rate of 0.1 Mrad.h$^{-1}$, the irradiation dose being 2.4 Mrad.

The experimental conditions of the absorption phase are as follows:
polymer quantity: 1 gram
solution volume: 8 ml
solvent: ethanol
codeine concentration: 22 g/100 ml
duration: 18 h
temperature: 50° C.

The codeine quantity absorbed is 52%. The desorption kinetics at variable pH are represented by curve $C_{14}$ of FIG. 6.

EXAMPLE 16

The polymer has the following composition: 45% butyl methacrylate, 45% heptyl methacrylate and 10% trimethylol propane trimethacrylate, whilst its grain size is 250 to 400 microns. The polymerization conditions are as defined in example 15. The experimental conditions for the absorption phase are the same as those for example 15.

The absorbed codeine quantity is 4.3%. The desorption kinetics at variable pH value are represented by curve $C_{15}$ of FIG. 6.

EXAMPLE 17

The polymer has the following composition: acrylamide 50% and polyethylene glycol diacrylate 50%, whilst its grain size is 250 to 400 microns.

It was obtained by polymerization in accordance with the conditions of example 15 and cross-linking by irradiation with a supplementary irradiation dose of 6 Mrad.

The experimental conditions of the absorption phase are the same as those of example 15.

The codeine quantity absorbed is 33.4%. The desorption kinetics at variable pH value are represented by curve $C_{16}$ of FIG. 6.

EXAMPLE 18

The following mixture of monomers is polymerized under γ radiation of Co$^{60}$ under the conditions of example 8: 47.5 parts by weight of methyl methacrylate, 47.5 parts by weight of butyl methacrylate and 5 parts by weight of polyethylene glycol diacrylate.

Ketoprofen absorption takes place under the same conditions as in example 8 on a powder with a grain size of 200 to 400 μm.

The absorption weight is 25% of ketoprofen. The desorption kinetics at constant pH of 7.4 are represented by curve $C_{17}$ of FIG. 7.

EXAMPLE 19

The mixture of the following monomers was polymerized under γ radiations of Co$^{60}$ under the conditions of example 8: 47.5 parts by weight of methyl methacrylate, 47.5 parts by weight of butyl methacrylate and 5 parts by weight of trimethylol propane trimethacrylate.

Ketoprofen absorption is effected under the same conditions as in example 8 on a powder of grain size 200 to 400 μm. The absorption rate is 19% of ketoprofen.

The desorption kinetics at constant pH of 7.4 are represented by curve $C_{18}$ of FIG. 8.

EXAMPLE 20

Codeine-Based Gelatin Capsule

The medicament quantity introduced into the capsule is 133 mg and contains 40 mg of codeine base. The support copolymer of example 2 is used. Grain size is 250 to 400 microns.

The composition of the capsule wall is as follows:
gelatin with dye containing 12 to 15% water
opacity obtained by adding titanium dioxide
metasulphite-type preservatives.

EXAMPLE 21

Codeine-Based Suppository 133 mg of the copolymer of example 2 with a grain size of 20 to 50 μm and containing 40 mg of codeine are suspended homogeneously in semisynthetic glycerides able to melt at 37° C. The suspension is poured into moulds and then cooled.

We claim:
1. A pharmaceutical composition comprising an inert support and codeine and/or 2-(3-benzoyphenyl)-propionic acid absorbed thereinto, wherein the inert support is constituted by a powder of a cross-linked copolymer of:
   30–80% by weight of a mono-unsaturated alkyl acrylate and/or alkyl methacrylate wherein the alkyl acrylate is selected from the group consisting of butyl, hexyl and heptylacrylates and the methacrylate is selected from the group consisting of methyl, ethyl, butyl, hexyl and heptylmethacrylates;
   5–68% by weight of acrylic and/or methacrylic acid; and
   2–15% by weight of bifunctional or trifunctional acrylate and/or methacrylate selected from the group consisting of polyethylene glycol diacrylate, trimethylol propane triacrylate and trimethylol propane trimethacrylate, said powder having a grain size of 20–700 microns.
2. A pharmaceutical composition according to claim 1, wherein said polyethylene glycol diacrylate is diethylene glycol diacrylate or tetraethylene glycol diacrylate.
3. A pharmaceutical composition according to claim 1, wherein the powder has a grain size of 100 to 400 micron.
4. A pharmaceutical composition according to claim 1, wherein the powder has a grain size of 20 to 50 micron.
5. A pharmaceutical composition according to claim 1, wherein the copolymer is a copolymer of butyl meth- acrylate, acrylic acid and trimethylol propane triacrylate.

6. A pharmaceutical composition according to claim 1, wherein the copolymer is a copolymer of butyl methacrylate, acrylic acid and tetraethylene glycol diacrylate.

7. A pharmaceutical composition according to claim 1, wherein the copolymer is a copolymer of heptyl methacrylate, acrylic acid and trimethylol propane trimethacrylate.

8. A pharmaceutical composition according to claim 1, wherein the copolymer is a copolymer of butyl methacrylate, acrylic acid and trimethylol propane trimethacrylate.

* * * * *